(12) United States Patent
Sato et al.

(10) Patent No.: US 7,119,107 B2
(45) Date of Patent: Oct. 10, 2006

(54) PYRIDONE DERIVATIVES

(75) Inventors: Nagaaki Sato, Tsukuba (JP); Tsuyoshi Nagase, Tsukuba (JP); Keita Nagai, Tsukuba (JP); Makoto Ando, Tsukuba (JP); Akio Kanatani, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/505,476

(22) PCT Filed: Mar. 14, 2003

(86) PCT No.: PCT/JP03/03115

§ 371 (c)(1),
(2), (4) Date: Oct. 27, 2004

(87) PCT Pub. No.: WO03/078422

PCT Pub. Date: Sep. 25, 2003

(65) Prior Publication Data

US 2005/0154025 A1    Jul. 14, 2005

(30) Foreign Application Priority Data

Mar. 15, 2002   (JP)  ............... 2002-073120

(51) Int. Cl.
 A61K 31/4439  (2006.01)
 C07D 401/14   (2006.01)
(52) U.S. Cl. .................... 514/333; 546/256
(58) Field of Classification Search ........... 546/256; 514/333
 See application file for complete search history.

(56) References Cited

FOREIGN PATENT DOCUMENTS

EP  1 264 826   12/2002
WO  88/04938   7/1988
WO  01/62738   8/2001

*Primary Examiner*—Patricia L. Morris
(74) *Attorney, Agent, or Firm*—Wenderoth, Lind & Ponack, L.L.P.

(57) ABSTRACT

A compound of the formula (I):

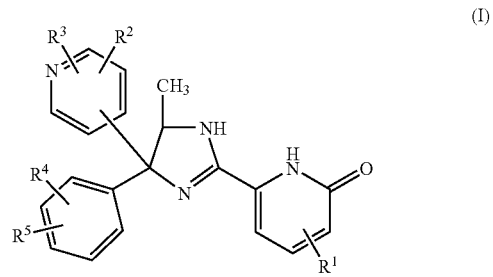

wherein $R^1$ is hydrogen, halogen, cyano, lower alkyl, halo-lower alkyl, hydroxy, lower alkoxy or aralkyloxy; $R^2$ and $R^3$ are each independently hydrogen, halogen or halo-lower alkyl; and $R^4$ and $R^5$ are each independently hydrogen or halogen, is useful as a pharmaceutical composition for the treatment of various diseases related to NPY, for example, cardiovascular disorders such as angina, acute or congestive heart failure, myocardial infarction, hypertension, nephropathy, electrolyte abnormality, vasospasm, etc., nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, gout, fatty liver, etc., genital or reproductive disorders such as infertility, preterm labor, sexual dysfunction, etc., gastrointestinal disorders, respiratory disorders, inflammatory diseases or glaucoma, and the like.

12 Claims, No Drawings

PYRIDONE DERIVATIVES

This application is a U.S. national stage of International Application No. PCT/JP03/03115 filed Mar. 14, 2003.

TECHNICAL FIELD

The present invention is useful in medical fields. In more detail, novel pyridone derivatives of the present invention have an effect as neuropeptide Y receptor antagonists and are useful as pharmaceutical compositions for the treatment of various kinds of cardiovascular disorders, central nervous system disorders, metabolic diseases, and the like.

BACKGROUND ART

Neuropeptide Y (hereinafter referred to as NPY), a peptide consisting of 36 amino acids, was first isolated from porcine brain by Tatemoto et al. in 1982 (NATURE, vol. 296, p. 659(1982)). NPY is widely distributed in central nervous system and peripheral nervous system, and plays various roles as one of the most abundant peptides in the nervous system. That is, NPY acts as an orexigenic substance in the central nervous system and markedly promotes fat accumulation via the mediation of secretion of various hormones or the action of the nervous system. It is known that continuous intracerebroventricular administration of NPY induces obesity and insulin resistance due to these actions (INTERNATIONAL JOURNAL OF OBESITY, vol. 19, p. 517(1995); Endocrinology, vol. 133, p. 1753(1993)). It is also known that NPY has central actions such as depression, anxiety, schizophrenia, pain, dementia, circadian rhythm control and the like (DRUGS, vol. 52, p. 371(1996); THE JOURNAL OF NEUROSCIENCE, vol. 18, p. 3014(1998)). Furthermore, in the periphery, NPY coexists with norepinephrine in sympathetic-nerve terminals and is related to the tonicity of the sympathetic nervous system. It is known that peripheral administration of NPY causes vasoconstriction and enhances the activities of other vasoconstrictive substances such as norepinephrine (BRITISH JOURNAL OF PHARMACOLOGY, vol. 95, p. 419(1988)). It is also reported that NPY could participate in the development of cardiac hypertrophy as a result of the sympathetic stimulation (PROCEEDINGS OF THE NATIONAL ACADEMY OF SCIENCES OF THE UNITED STATES OF AMERICA, vol. 97, p. 1595(2000)).

On the other hand, it is reported that NPY is also involved in the secretory function of sexual hormones and growth hormone, sexual behavior and reproductive function, gastrointestinal motility, bronchoconstriction, inflammation and alcohol preference (LIFE SCIENCE, vol. 55, p. 551(1994); THE JOURNAL OF ALLERGY AND CLINICAL IMMUNOLOGY, vol. 101, p. S345(1998); NATURE, vol. 396, p. 366(1998)).

NPY has a variety of pharmacological effects resulting from NPY binding to some NPY receptors to which peptide YY and pancreatic polypeptide, which are the analogs of NPY, also bind. It is known that these pharmacological effects of NPY are mediated by the action of at least five receptors with or without synergistic interactions (TRENDS IN NEUROSCIENCES, vol. 20, p. 294(1997)).

It is reported that the central effects mediated by NPY Y1 receptor include remarkable orexigenic effect (ENDOCRINOLOGY, vol. 137, p. 3177(1996); ENDOCRINOLOGY, vol. 141, p. 1011(2000)). Further, NPY Y1 receptor is reported to be involved in anxiety and pain (NATURE, vol. 259, p. 528(1993); BRAIN RESEARCH, vol. 859, p. 361 (2000). In addition, the pressor effect mediated by the strong vasoconstrictor action in the periphery is also reported (FEBS LETTERS, vol. 362, p. 192(1995); NATURE MEDICINE, vol. 4, p. 722(1998)).

It is known that the effects mediated by NPY Y2 receptor include an inhibitory effect on the release of various neurotransmitters in the sympathetic nerve endings (BRITISH JOURNAL OF PHARMACOLOGY, vol. 102, p. 41(1991); SYNAPSE, vol. 2, p. 299(1988)). In periphery, NPY Y2 causes constriction of blood vessel or vas deferens directly or via the control of release of various neurotransmitters (THE JOURNAL OF PHARMACOLOGY AND EXPERIMENTAL THERAPEUTICS, vol. 261, p. 863(1992); BRITISH JOURNAL OF PHARMACOLOGY, vol. 100, p. 190 (1990)). Inhibition of lipolysis in adipose tissues is also known (ENDOCRINOLOGY, vol. 131, p. 1970(1992)). Further, inhibition of ion secretion in the gastro-intestinal tract is reported (BRITISH JOURNAL OF PHARMACOLOGY, vol. 101, p. 247(1990)). On the other hand, the effects on the central nervous system functions such as memory, anxiety and the like are also known (BRAIN RESEARCH, vol. 503, p. 73(1989); PEPTIDES, vol. 19, p. 359(1998)).

It is reported that NPY Y3 receptor exists mainly in brainstem and heart, and is related to the regulation of blood pressure and heart rate (THE JOURNAL OF PHARMACOLOGY AND EXPERIMENTAL THERAPEUTICS, vol. 258, p. 633(1991); PEPTIDES, vol. 11, p. 545(1990)). It is also known that NPY Y3 is involved in the control of catecholamine secretion in adrenal gland (THE JOURNAL OF PHARMACOLOGY AND EXPERIMENTAL THERAPEUTICS, vol. 244, p. 468(1988); LIFE SCIENCE, vol. 50, p. PL7(1992)).

NPY Y4 receptor has high affinity for pancreatic polypeptide in particular. As for the pharmacological effects of NPY Y4, inhibition of pancreatic exocrine secretion and gastro-intestinal motility is reported (GASTROENTEROLOGY, vol. 85, p. 1411(1983)). Further, it is reported that NPY enhances the secretion of sexual hormones in the central nervous system (ENDOCRINOLOGY, vol. 140, p. 5171 (1999)).

As for the effects mediated by NPY Y5 receptor, fat accumulation effects including orexigenic effect are prominent (NATURE, vol. 382, p. 168(1996); AMERICAN JOURNAL OF PHYSIOLOGY, vol. 277, p. R1428(1999)). It is also reported that the NPY Y5 receptor mediates some CNS effects, such as seizure and epilepsy, or pain and morphine withdrawal symptoms, and the control of circadian rhythm (NATURE MEDICINE, vol. 3, p. 761(1997); PROCEEDINGS OF THE NATIONAL ACADEMY OF SCIENCES OF THE UNITED STATES OF AMERICA, vol. 96, p. 13518(1999); THE JOURNAL OF PHARMACOLOGY AND EXPERIMENTAL THERAPEUTICS, vol. 284, p. 633(1998); THE JOURNAL OF NEUROSCIENCE, vol. 21, p. 5367(2001). In addition, diuretic effect and hypoglicemic effect in the periphery are reported (BRITISH JOURNAL OF PHARMACOLOGY, vol. 120, p. 1335(1998); ENDOCRINOLOGY, vol. 139, p. 3018(1998)). NPY is also reported to enhance cardiac hypertrophy as a result of the sympathetic accentuation (PROCEEDINGS OF THE NATIONAL ACADEMY OF SCIENCES OF THE UNITED STATES OF AMERICA, vol. 97, p. 1595(2000)).

The effects of NPY are expressed when NPY binds to the NPY receptors in the central or peripheral nervous system. Therefore, the action of NPY can be prevented by blocking its binding to NPY receptors. Accordingly, it is expected that substances antagonize NPY binding to NPY receptors may be useful for the prophylaxis or treatment of various diseases related to NPY, for example, cardiovascular disorders such as angina, acute or congestive heart failure, myocardial infarction, hypertension, nephropathy, electrolyte abnormality, vasospasm, etc., nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, gout, fatty liver, etc., genital or reproductive disorders such as infertility, preterm labor, sexual dysfunction, etc., gastro-intestinal disorders, respiratory disorders, inflammatory diseases or glaucoma, and the like. (TRENDS IN PHARMACOLOGICAL SCIENCES, vol. 15, p. 153(1994); LIFE SCIENCE, vol. 55, p. 551(1994); DRUGS, vol. 52, p. 371(1996); THE JOURNAL OF ALLERGY AND CLINICAL IMMUNOLOGY, vol. 101, p. S345(1998); NATURE, vol. 396, p. 366(1998); THE JOURNAL OF PHARMACOLOGY AND EXPERIMENTAL THERAPEUTICS, vol. 284, p. 633(1998); TRENDS IN PHARMACOLOGICAL SCIENCES, vol. 20, p. 104 (1999); PROCEEDINGS OF THE NATIONAL ACADEMY OF SCIENCES OF THE UNITED STATES OF AMERICA, vol. 97, p. 1595(2000); THE JOURNAL OF NEUROSCIENCE, vol. 21, p. 5367(2001); PHARMACOLOGY & THERAPEUTICS, vol. 65, p. 397(1995); ENDOCRINOLOGY, vol. 140, p. 4046(1999); AMERICAN JOUNARL OF PHYSIOLOGY, vol. 280, p. R1061(2001); AMERICAN JOUNARL OF PHYSIOLOGY, vol. 278, p. R1627(2000); CURRENT OPINION IN CLINICAL NUTRITION AND METABOLIC CARE, vol. 2, p. 425 (1999); CURRENT RHEUMATOLOGY REPORTS, vol. 3, p. 101(2001), AMERICAN JOURNAL OF RESPIRATORY AND CRITICAL CARE MEDICINE, vol. 165, p. 1217 (2002).

It was recently found that, as a result of the study by the present inventors, certain NPY receptor antagonists are useful for the prophylaxis or treatment of hypercholesterolemia, hyperlipidemia and arteriosclerosis (International application publication WO99/27965).

International application publication WO01/62738 discloses a variety of imidazoline derivatives, and mentions that the derivatives have excellent NPY receptor antagonistic actions and also show excellent pharmacokinetics such as transport into brain or transport to cerebrospinal fluid, etc. However, the said literatures do not specifically describe the compounds of the present invention.

DISCLOSURE OF INVENTION

The object of the present invention is to provide novel medicines which have NPY antagonistic actions.

The present inventors have discovered that compounds of the formula (I):

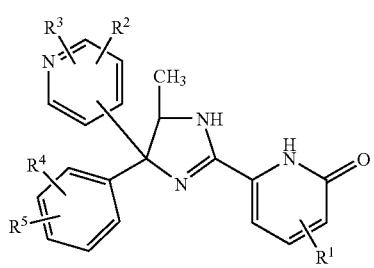

(I)

wherein $R^1$ is hydrogen, halogen, cyano, lower alkyl, halo-lower alkyl, hydroxy, lower alkoxy or aralkyloxy; $R^2$ and $R^3$ are each independently hydrogen, halogen or halo-lower alkyl; and $R^4$ and $R^5$ are each independently hydrogen or halogen, provided that when $R^1$ is hydrogen, a group of the formula:

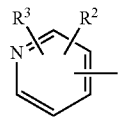

and a group of the formula:

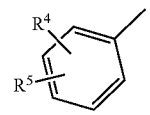

do not simultaneously represent 6-fluoro-3-pyridyl and 4-fluorophenyl, respectively, have NPY antagonistic actions, show excellent pharmacokinetics such as transport into brain or transport to cerebrospinal fluid, etc., and are also very safe, and thereby they completed the present invention.

The compounds (I) of the present invention have NPY antagonistic actions, show excellent pharmacokinetics such as transport into brain or transport to cerebrospinal fluid, etc. and are very safe, thus they are useful as pharmaceutical compositions for the treatment of various diseases related to NPY, for example, cardiovascular disorders such as angina, acute or congestive heart failure, myocardial infarction, hypertension, nephropathy, electrolyte abnormality, vasospasm, etc., nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, gout, fatty liver, etc., genital or reproductive disorders such as infertility, preterm labor, sexual dysfunction, etc., gastro-intestinal disorders, respiratory disorders, inflammatory diseases or glaucoma, and the like.

The compounds (I) of the present invention are particularly useful as pharmaceutical compositions for the treatment of bulimia, obesity, diabetes and the like.

The present invention relates to the compounds of the formula (I) or the salts thereof, and the production methods and the use thereof.

The means of terms used in the present specification are defined, and more detailed description of this invention is described below.

"Halogen" refers to fluorine, chlorine, bromine and iodine.

"Lower alkyl" refers to a straight- or branched-chain alkyl group of C1 to C6, and its examples are methyl, ethyl, propyl, isopropyl, butyl, isobutyl, sec-butyl, tert-butyl, pentyl, isopentyl, hexyl, isohexyl and the like.

"Halo-lower alkyl" refers to said lower alkyl substituted with identically or differently one, two or more, preferably one to three said halogen at the substitutable, arbitrary position(s), and its examples are fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl and the like.

"Lower alkoxy" refers to a straight- or branched-chain alkoxy group of C1 to C6, and its examples are methoxy, ethoxy, propoxy, isopropoxy, butoxy, sec-butoxy, isobutoxy, tert-butoxy, pentyloxy, isopentyloxy, hexyloxy, isohexyloxy, and the like.

"Aryl" refers to phenyl, naphthyl and the like.

"Aralkyl" refers to said lower alkyl substituted with one, two or more, preferably one said aryl at the substitutable, arbitrary position(s), and its examples are benzyl, 1-phenylethyl, phenethyl, 1-naphthylmethyl, 2-naphthylmethyl and the like.

"Aralkyloxy" refers to aralkyloxy containing said aralkyl, and its examples are benzyloxy, 1-phenylethyloxy, phenethyloxy, 1-naphthylmethyloxy, 2-naphthylmethyloxy and the like.

The salts of the compounds of the formula (I) refer to pharmaceutically acceptable, common salts, and examples thereof are acid addition salts to basic heterocyclyl and the like.

Said acid addition salts include salts with inorganic acids (e.g. hydrochloric acid, sulfuric acid, nitric acid, phosphoric acid, perchloric acid), salts with organic acids (e.g. maleic acid, fumaric acid, tartaric acid, citric acid, ascorbic acid, trifluoroacetic acid), salts with sulfonic acids (e.g. methanesulfonic acid, isethionic acid, benzenesulfonic acid, p-toluenesulfonic acid) and the like.

"A pharmaceutical composition for treatment" refers to a medicament which is employed for the treatment and/or prophylaxis of various diseases.

In order to disclose the aforesaid compounds of the formula (I) of the present invention more specifically, the various symbols used in the formula (I) are explained in more detail by presenting preferred embodiments.

$R^1$ is hydrogen, halogen, cyano, lower alkyl, halo-lower alkyl, hydroxy, lower alkoxy or aralkyloxy, and can be present at a substitutable, arbitrary position on the group of the formula (a):

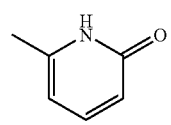

(a)

in the formula (I).

$R^2$ and $R^3$ are each independently hydrogen, halogen or halo-lower alkyl, and can be present at substitutable, arbitrary position(s) on the pyridyl group of the formula (b):

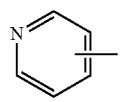

(b)

in the formula (I). Also, said pyridyl group can bind to 4-position of the adjacent imidazoline ring at an arbitrary, bondable position.

$R^4$ and $R^5$ are each independently hydrogen or halogen, and can be present at substitutable, arbitrary position(s) on the phenyl group binding to 4-position of the imidazoline ring.

On the other hand, the compound of the formula (I), wherein, when $R^1$ is hydrogen, a group of the formula:

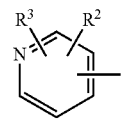

and a group of the formula:

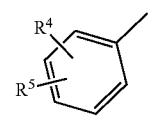

simultaneously represent 6-fluoro-3-pyridyl and 4-fluorophenyl, respectively, is excluded from the scope of the present invention.

The compounds of the formula (I) include compounds of the formula (Ia):

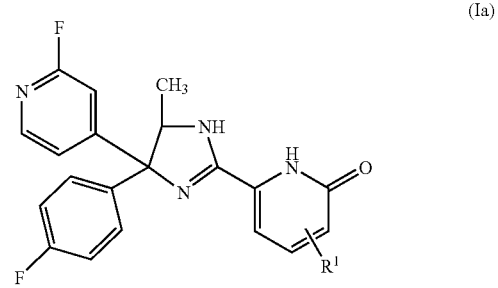

(Ia)

wherein $R^1$ has the same meaning as defined above, and compounds of the formula (Ib):

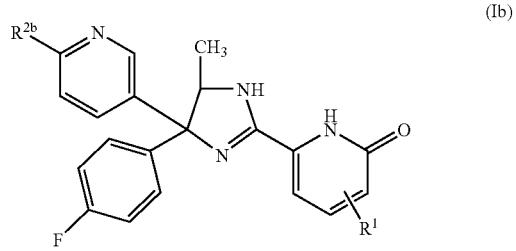

(Ib)

wherein $R^{2b}$ is halogen or halo-lower alkyl; and $R^1$ has the same meaning as defined above, provided that when $R^1$ is hydrogen, $R^{2b}$ is not fluorine.

The compounds of the formula (Ia) include compounds of the formula (Ia-1):

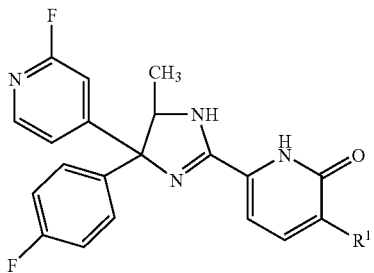

(Ia-1)

wherein R¹ has the same meaning as defined above.

Among the compounds of the formula (Ia) or formula (Ia-1), preferable examples include compounds in which R¹ is hydrogen, halogen or hydroxy, more preferably hydroxy.

In the formula (Ia) or formula (Ia-1), halogen as R¹ is preferably, for example, fluorine and the like.

The compounds of the formula (Ib) include compounds of the formula (Ib-1):

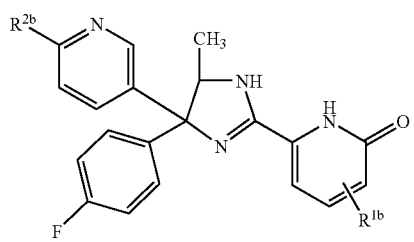

(Ib-1)

wherein $R^{1b}$ is halogen, cyano, lower alkyl, halo-lower alkyl, hydroxy, lower alkoxy or aralkyloxy; and $R^{2b}$ has the same meaning as defined above.

Among the compounds of the formula (Ib-1), preferable examples include compounds in which $R^{2b}$ is fluorine or trifluoromethyl, and more preferable examples include compounds in which $R^{2b}$ is fluorine or trifluoromethyl and additionally $R^{1b}$ is halogen or lower alkyl.

The compounds of the formula (Ib-1) include compounds of the formula (Ib-2):

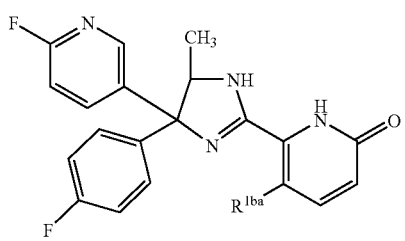

(Ib-2)

wherein $R^{1ba}$ is halogen, and compounds of the formula (Ib-3):

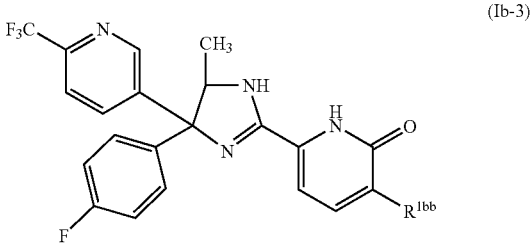

(Ib-3)

wherein $R^{1bb}$ is lower alkyl.

Among the compounds of the formula (Ib-2), preferable examples include compounds in which the halogen as $R^{1ba}$ is fluorine.

Among the compounds of the formula (Ib-3), preferable examples include compounds in which the lower alkyl as $R^{1bb}$ is methyl.

The compounds of the present invention may include stereoisomers such as optical isomers, diastereoisomers and geometrical isomers, or tautomers depending upon the mode of substituents. The compounds of the present invention include all the stereoisomers, tautomers and their mixtures.

Also included within the scope of the invention are polymorphs, hydrates and solvates of the compounds of the present invention.

The present invention also includes prodrugs of the compounds of the present invention within its scope. In general, such prodrugs are functional derivatives of the compounds of the present invention which can be readily converted in vivo into the required compound. Thus, in the treatment methods for various diseases according to the present invention, the term "administering" shall encompass not only administration of the compound specified in this disclosure but also administration of a compound which is converted in vivo into the specified compound when it is administered to a patient. Conventional procedures for selection and preparation of suitable prodrug derivatives are described, for example, in "Design of Prodrugs," ed. H. Bundgaard, Elsevier (1985), which are referred to and entirely incorporated in this specification. The metabolites of these compounds include active compounds which are produced upon introduction of compounds of the present invention into the biological milieu, and they are encompassed in the scope of the present invention.

The specific compounds of the formula (I) are, for example,

6-[(4R,5S)-4-(4-fluorophenyl)-4-(2-fluoro-4-pyridyl)-5-methyl-2-imidazolin-2-yl]-2(1H)-pyridinone,
6-[(4S,5S)-4-(4-fluorophenyl)-4-(2-fluoro-4-pyridyl)-5-methyl-2-imidazolin-2-yl]-2(1H)-pyridinone,
6-[(4R,5R)-4-(4-fluorophenyl)-4-(2-fluoro-4-pyridyl)-5-methyl-2-imidazolin-2-yl]-2(1H)-pyridinone,
6-[(4S,5R)-4-(4-fluorophenyl)-4-(2-fluoro-4-pyridyl)-5-methyl-2-imidazolin-2-yl]-2(1H)-pyridinone,
6-[(4R,5S)-4-(4-fluorophenyl)-4-(6-trifluoromethyl-3-pyridyl)-5-methyl-2-imidazolin-2-yl]-2(1H)-pyridinone,
6-[(4S,5S)-4-(4-fluorophenyl)-4-(6-trifluoromethyl-3-pyridyl)-5-methyl-2-imidazolin-2-yl]-2(1H)-pyridinone,
6-[(4R,5S)-4-(4-fluorophenyl)-4-(5-fluoro-2-pyridyl)-5-methyl-2-imidazolin-2-yl]-2(1H)-pyridinone, 6-[(4S,5S)-4-(4-fluorophenyl)-4-(5-fluoro-2-pyridyl)-5-methyl-2-imidazolin-2-yl]-2(1H)-pyridinone,
6-[(4R,5S)-4-(4-fluorophenyl)-4-(3-fluoro-4-pyridyl)-5-methyl-2-imidazolin-2-yl]-2(1H)-pyridinone,
6-[(4S,5S)-4-(4-fluorophenyl)-4-(3-fluoro-4-pyridyl)-5-methyl-2-imidazolin-2-yl]-2(1H)-pyridinone,
6-[(4R,5S)-4-(4-fluorophenyl)-4-(3-fluoro-2-pyridyl)-5-methyl-2-imidazolin-2-yl]-2(1H)-pyridinone,
6-[(4S,5S)-4-(4-fluorophenyl)-4-(3-fluoro-2-pyridyl)-5-methyl-2-imidazolin-2-yl]-2(1H)-pyridinone,
3-chloro-6-[(4R,5S)-4-(4-fluorophenyl)-4-(6-fluoro-3-pyridyl)-5-methyl-2-imidazolin-2-yl]-2(1H)-pyridinone,
3-chloro-6-[(4S,5S)-4-(4-fluorophenyl)-4-(6-fluoro-3-pyridyl)-5-methyl-2-imidazolin-2-yl]-2(1H)-pyridinone,
6-[(4R,5S)-4-(3-bromo-4-fluorophenyl)-4-(2-fluoro-4-pyridyl)-5-methyl-2-imidazolin-2-yl]-2(1H)-pyridinone,
6-[(4S,5S)-4-(3-bromo-4-fluorophenyl)-4-(2-fluoro-4-pyridyl)-5-methyl-2-imidazolin-2-yl]-2(1H)-pyridinone,
4-chloro-6-[(4R,5S)-4-(4-fluorophenyl)-4-(2-fluoro-4-pyridyl)-5-methyl-2-imidazolin-2-yl]-2(1H)-pyridinone,
4-chloro-6-[(4S,5S)-4-(4-fluorophenyl)-4-(2-fluoro-4-pyridyl)-5-methyl-2-imidazolin-2-yl]-2(1H)-pyridinone,
4-cyano-6-[(4R,5S)-4-(4-fluorophenyl)-4-(6-fluoro-3-pyridyl)-5-methyl-2-imidazolin-2-yl]-2(1H)-pyridinone,
4-cyano-6-[(4S,5S)-4-(4-fluorophenyl)-4-(6-fluoro-3-pyridyl)-5-methyl-2-imidazolin-2-yl]-2(1H)-pyridinone,
6-[(4R,5S)-4-(3,4-difluorophenyl)-4-(2-fluoro-4-pyridyl)-5-methyl-2-imidazolin-2-yl]-2(1H)-pyridinone,
6-[(4S,5S)-4-(3,4-difluorophenyl)-4-(2-fluoro-4-pyridyl)-5-methyl-2-imidazolin-2-yl]-2(1H)-pyridinone,
6-[(4R,5S)-4-(4-fluorophenyl)-4-(2-fluoro-4-pyridyl)-5-methyl-2-imidazolin-2-yl]-3-hydroxy-2(1H)-pyridinone,
6-[(4S,5S)-4-(4-fluorophenyl)-4-(2-fluoro-4-pyridyl)-5-methyl-2-imidazolin-2-yl]-3-hydroxy-2(1H)-pyridinone,
6-[(4R,5S)-4-(4-fluorophenyl)-4-(2-fluoro-4-pyridyl)-5-methyl-2-imidazolin-2-yl]-3-methyl-2(1H)-pyridinone,
6-[(4S,5S)-4-(4-fluorophenyl)-4-(2-fluoro-4-pyridyl)-5-methyl-2-imidazolin-2-yl]-3-methyl-2(1H)-pyridinone,
3-fluoro-6-[(4R,5S)-4-(4-fluorophenyl)-4-(2-fluoro-4-pyridyl)-5-methyl-2-imidazolin-2-yl]-2(1H)-pyridinone,
3-fluoro-6-[(4S,5S)-4-(4-fluorophenyl)-4-(2-fluoro-4-pyridyl)-5-methyl-2-imidazolin-2-yl]-2(1H)-pyridinone,
3-benzyloxy-6-[(4R,5S)-4-(4-fluorophenyl)-4-(2-fluoro-4-pyridyl)-5-methyl-2-imidazolin-2-yl]-2(1H)-pyridinone,
3-benzyloxy-6-[(4S,5S)-4-(4-fluorophenyl)-4-(2-fluoro-4-pyridyl)-5-methyl-2-imidazolin-2-yl]-2(1H)-pyridinone,
3-fluoro-6-[(4R,5S)-4-(4-fluorophenyl)-4-(6-fluoro-3-pyridyl)-5-methyl-2-imidazolin-2-yl]-2(1H)-pyridinone,
3-fluoro-6-[(4S,5S)-4-(4-fluorophenyl)-4-(6-fluoro-3-pyridyl)-5-methyl-2-imidazolin-2-yl]-2(1H)-pyridinone,
6-[(4R,5S)-4-(4-fluorophenyl)-4-(2-fluoro-4-pyridyl)-5-methyl-2-imidazolin-2-yl]-3-trifluoromethyl-2(1H)-pyridinone,
6-[(4S,5S)-4-(4-fluorophenyl)-4-(2-fluoro-4-pyridyl)-5-methyl-2-imidazolin-2-yl]-3-trifluoromethyl-2(1H)-pyridinone,
6-[(4R,5S)-4-(4-fluorophenyl)-4-(6-fluoro-3-pyridyl)-5-methyl-2-imidazolin-2-yl]-3-methyl-2(1H)-pyridinone,
6-[(4S,5S)-4-(4-fluorophenyl)-4-(6-fluoro-3-pyridyl)-5-methyl-2-imidazolin-2-yl]-3-methyl-2(1H)-pyridinone,
5-fluoro-6-[(4R,5S)-4-(4-fluorophenyl)-4-(2-fluoro-4-pyridyl)-5-methyl-2-imidazolin-2-yl]-2(1H)-pyridinone,
5-fluoro-6-[(4S,5S)-4-(4-fluorophenyl)-4-(2-fluoro-4-pyridyl)-5-methyl-2-imidazolin-2-yl]-2(1H)-pyridinone,
5-fluoro-6-[(4R,5S)-4-(4-fluorophenyl)-4-(6-fluoro-3-pyridyl)-5-methyl-2-imidazolin-2-yl]-2(1H)-pyridinone,
5-fluoro-6-[(4S,5S)-4-(4-fluorophenyl)-4-(6-fluoro-3-pyridyl)-5-methyl-2-imidazolin-2-yl]-2(1H)-pyridinone,
3-fluoro-6-[(4R,5S)-4-(4-fluorophenyl)-4-(6-trifluoromethyl-3-pyridyl)-5-methyl-2-imidazolin-2-yl]-2(1H)-pyridinone,
3-fluoro-6-[(4S,5S)-4-(4-fluorophenyl)-4-(6-trifluoromethyl-3-pyridyl)-5-methyl-2-imidazolin-2-yl]-2(1H)-pyridinone,
6-[(4R,5S)-4-(4-fluorophenyl)-4-(6-trifluoromethyl-3-pyridyl)-5-methyl-2-imidazolin-2-yl]-3-methyl-2(1H)-pyridinone,
6-[(4S,5S)-4-(4-fluorophenyl)-4-(6-trifluoromethyl-3-pyridyl)-5-methyl-2-imidazolin-2-yl]-3-methyl-2(1H)-pyridinone,
6-[(4R,5S)-4-(4-fluorophenyl)-4-(2-fluoro-4-pyridyl)-5-methyl-2-imidazolin-2-yl]-5-hydroxy-2(1H)-pyridinone,
6-[(4S,5S)-4-(4-fluorophenyl)-4-(2-fluoro-4-pyridyl)-5-methyl-2-imidazolin-2-yl]-5-hydroxy-2(1H)-pyridinone,
6-[(4R,5S)-4-(4-fluorophenyl)-4-(2-fluoro-4-pyridyl)-5-methyl-2-imidazolin-2-yl]-4-methyl-2(1H)-pyridinone,
6-[(4S,5S)-4-(4-fluorophenyl)-4-(2-fluoro-4-pyridyl)-5-methyl-2-imidazolin-2-yl]-4-methyl-2(1H)-pyridinone,
5-fluoro-6-[(4R,5S)-4-(4-fluorophenyl)-4-(6-trifluoromethyl-3-pyridyl)-5-methyl-2-imidazolin-2-yl]-2(1H)-pyridinone,
5-fluoro-6-[(4S,5S)-4-(4-fluorophenyl)-4-(6-trifluoromethyl-3-pyridyl)-5-methyl-2-imidazolin-2-yl]-2(1H)-pyridinone,
3-chloro-6-[(4R,5S)-4-(4-fluorophenyl)-4-(6-trifluoromethyl-3-pyridyl)-5-methyl-2-imidazolin-2-yl]-2(1H)-pyridinone,
3-chloro-6-[(4S,5S)-4-(4-fluorophenyl)-4-(6-trifluoromethyl-3-pyridyl)-5-methyl-2-imidazolin-2-yl]-2(1H)-pyridinone,
6-[(4R,5S)-4-(3-bromo-4-fluorophenyl)-4-(6-trifluoromethyl-3-pyridyl)-5-methyl-2-imidazolin-2-yl]-3-methyl-2(1H)-pyridinone,
6-[(4S,5S)-4-(3-bromo-4-fluorophenyl)-4-(6-trifluoromethyl-3-pyridyl)-5-methyl-2-imidazolin-2-yl]-3-methyl-2(1H)-pyridinone,
6-[(4R,5S)-4-(4-fluorophenyl)-4-(2-fluoro-4-pyridyl)-5-methyl-2-imidazolin-2-yl]-3-methyl-2(1H)-pyridinone,
6-[(4S,5S)-4-(4-fluorophenyl)-4-(2-fluoro-4-pyridyl)-5-methyl-2-imidazolin-2-yl]-3-methyl-2(1H)-pyridinone,
6-[(4R,5S)-4-(3-bromo-4-fluorophenyl)-4-(6-fluoro-3-pyridyl)-5-methyl-2-imidazolin-2-yl]-5-fluoro-2(1H)-pyridinone,
6-[(4S,5S)-4-(3-bromo-4-fluorophenyl)-4-(6-fluoro-3-pyridyl)-5-methyl-2-imidazolin-2-yl]-5-fluoro-2(1H)-pyridinone,
5-chloro-6-[(4R,5S)-4-(4-fluorophenyl)-4-(6-fluoro-3-pyridyl)-5-methyl-2-imidazolin-2-yl]-2(1H)-pyridinone,
5-chloro-6-[(4S,5S)-4-(4-fluorophenyl)-4-(6-fluoro-3-pyridyl)-5-methyl-2-imidazolin-2-yl]-2(1H)-pyridinone,
6-[(4R,5S)-4-(4-fluorophenyl)-4-(6-fluoro-3-pyridyl)-5-methyl-2-imidazolin-2-yl]-5-methyl-2(1H)-pyridinone,
6-[(4S,5S)-4-(4-fluorophenyl)-4-(6-fluoro-3-pyridyl)-5-methyl-2-imidazolin-2-yl]-5-methyl-2(1H)-pyridinone,
6-[(4R,5S)-4-(6-difluoromethyl-3-pyridyl)-4-(4-fluorophenyl)-5-methyl-2-imidazolin-2-yl]-2(1H)-pyridinone,
6-[(4S,5S)-4-(6-difluoromethyl-3-pyridyl)-4-(4-fluorophenyl)-5-methyl-2-imidazolin-2-yl]-2(1H)-pyridinone, and the like, among which the preferable examples are 6-[(4R,5S)-4-(4-fluorophenyl)-4-(2-fluoro-4-pyridyl)-5-methyl-2-imidazolin-2-yl]-2(1H)-pyridinone, 5-fluoro-6-[(4S,5S)-4-(4-fluorophenyl)-4-(6-fluoro-3-pyridyl)-5-methyl-2-imidazolin-2-yl]-2(1H)-pyridinone, 6-[(4R,5S)-4-(4-fluorophenyl)-4-(6-trifluoromethyl-3-pyridyl)-5-methyl-2-imidazolin-2-yl]-3-methyl-2(1H)-pyridinone and the like.

The processes for preparing the compounds of the present invention are illustrated as follows.

The compounds (I) of the present invention can be prepared, for example, by the following Production Processes or the methods shown in Examples, but production methods of the compounds (I) of the present invention are not limited to these embodiments.

Production Process 1

The compound of the formula (I) can be prepared by reacting a compound of the formula (II):

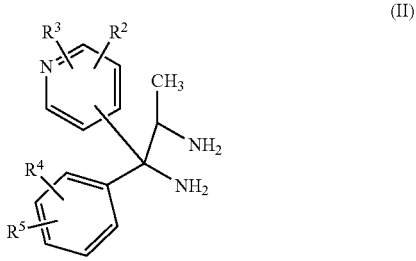

(II)

wherein $R^2$, $R^3$, $R^4$ and $R^5$ have each the same meaning as defined above, with an acid addition salt of a compound represented by the formula (III):

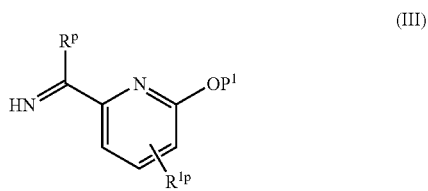

(III)

wherein $P^1$ is hydrogen or a hydroxy-protecting group; $R^{1p}$ is hydrogen, halogen, cyano, lower alkyl, halo-lower alkyl, lower alkoxy, aralkyloxy or optionally protected hydroxy; and $R^p$ is amino or lower alkoxy, to produce a compound of the formula (IV):

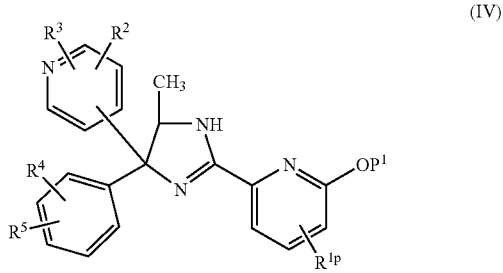

(IV)

wherein $P^1$, $R^{1p}$, $R^2$, $R^3$, $R^4$ and $R^5$ have each the same meaning as defined above, and optionally removing the protecting group(s) from the compound (IV).

In the above reaction, the reaction is carried out after the hydroxy group which does not participate in the reaction is appropriately protected with a hydroxy-protecting group, and said protecting group may be removed after completion of the reaction.

The "hydroxy-protecting group" includes, for example, lower alkylsilyl (e.g. trimethylsilyl, tert-butyldimethylsilyl); lower alkoxymethyl (e.g. methoxymethyl, 2-methoxyethoxymethyl); tetrahydropyranyl; trimethylsilylethoxymethyl; aralkyl (e.g. benzyl, p-methoxybenzyl, 2,3-dimethoxybenzyl, o-nitrobenzyl, p-nitrobenzyl, trityl); and acyl (e.g. formyl, acetyl), among which the preferable examples are methoxymethyl, tetrahydropyranyl, trityl, trimethylsilylethoxymethyl, tert-butyldimethylsilyl, acetyl and the like.

The reaction between a compound of the formula (II) and an acid addition salt of a compound represented by the formula (III) is usually carried out by employing 1 mole to excess moles, preferably 1 mole to 5 moles of an acid addition salt of the compound (III), relative to 1 mole of the compound (II).

A preferable example of the acid addition salt of the compound (III) is hydrochloride and the like.

The reaction is usually carried out in an inert solvent, and preferable examples of such solvent are alcohols (e.g. methanol, ethanol), dimethylformamide, dimethyl sulfoxide, etc. or a mixture thereof and the like.

The reaction temperature is usually from −30° C. to 200° C., preferably from 0° C. to 150° C.

The reaction time is usually 30 minutes to 7 days, preferably 2 hours to 5 days.

Usual workup procedures are applied after completion of the reaction to obtain a crude product of a compound of the formula (IV). The resulting compound of the formula (IV) is, with or without purification according to the common method, subjected to optional removal of the protecting group(s) for the hydroxy group, whereby a compound of the formula (I) can be prepared.

Although the method for the removal of said protecting groups depends upon the kinds of the protecting groups, the stability of a desired compound (I), etc., it is carried out by, for example, solvolysis using an acid or a base, that is, a method wherein, for example, 0.01 mole to a large excess of an acid, preferably trifluoroacetic acid, formic acid, hydrochloric acid and the like, or an equivalent mole to a large excess of a base, preferably potassium hydroxide, calcium hydroxide and the like is acted on; a chemical reduction using a metal hydride complex; or a catalytic reduction using a palladium-carbon catalyst, a Raney-nickel catalyst, etc., according to, for example, a method described in the literature (Protective Groups in Organic Synthesis, T. W. Greene, John Wiley & Sons, (1981)) or its similar methods.

Production Process 2

The compound of the formula (I) can be prepared by reacting a compound of the formula (II):

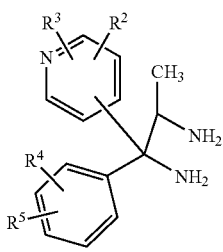

wherein $R^2$, $R^3$, $R^4$ and $R^5$ have each the same meaning as defined above, with a compound of the formula (V):

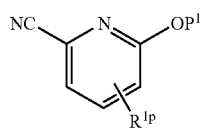

wherein $P^1$ and $R^{1p}$ have each the same meaning as defined above, to produce a compound of the formula (IV):

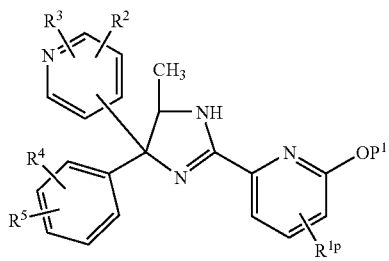

wherein $P^1$, $R^{1p}$, $R^2$, $R^3$, $R^4$ and $R^5$ have each the same meaning ng as defined above, and opt ionally removing the protecting group (s) from the compound (IV).

The reaction between a compound of the formula (II) and a compound of the formula (V) is usually carried out by employing 0.5 to 5 moles, preferably 0.7 to 3 moles of a compound (V), relative to 1 mole of compound (II).

The reaction is usually carried out in the absence of a solvent or in the presence of an inert solvent, and preferable examples of such inert solvent are benzene, toluene, xylene, methylene chloride, chloroform, hexane and a mixture thereof, and the like.

The reaction temperature is usually from −20° C. to the boiling point of the solvent used in the reaction, preferably from 0° C. to 200° C.

The reaction time is usually 30 minutes to 3 days, preferably 3 hours to 24 hours.

The above reaction is preferably carried out in the presence of a catalytic amount of a Lewis acid. Examples of such Lewis acid are scandium trifluoromethanesulfonate, ytterbium trifluoromethanesulfonate, lanthanum trifluoromethanesulfonate and the like.

The amount of said Lewis acid used is usually 1 mole % to 50 mole %, preferably 3 mole % to 30 mole %, relative to 1 mole of the compound (II).

When the reaction is carried out in the presence of a Lewis acid, the reaction is effected in the absence of a solvent or preferably in the presence of a solvent such as methylene chloride, chloroform, benzene, toluene, xylene or a mixture thereof.

The reaction temperature is usually from 0° C. to the boiling point of the solvent used in the reaction, preferably from room temperature to 150° C.

The reaction time is usually one hour to 7 days, preferably 2 hours to 24 hours.

A compound of the formula (I) can be produced by working up a reaction mixture in the usual way after removal of the said protecting group(s) when the product has a protecting group after completion of the reaction, or by working up the mixture directly in the usual way when the protecting group is absent.

The removal of the protecting group(s) and the workup procedure may be carried out according to the method described in the above Production Process 1.

Production Process 3

The compound of the formula (I) can be prepared by reacting a compound of the formula (II):

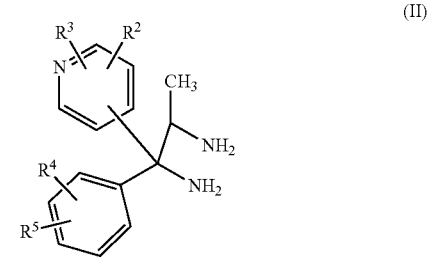

wherein $R^2$, $R^3$, $R^4$ and $R^5$ have each the same meaning as defined above, with a compound of the formula (VI):

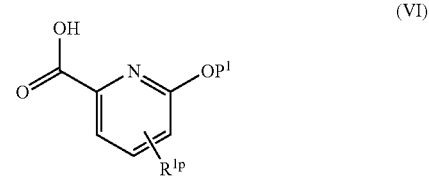

wherein $P^1$ and $R^{1p}$ have each the same meaning as defined above, to produce a compound of the formula (VII):

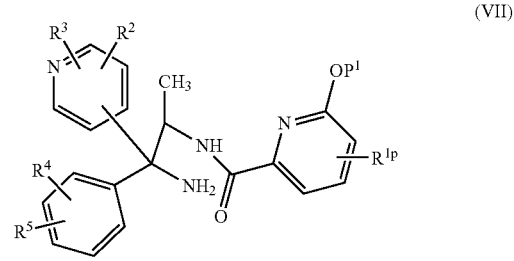

wherein $P^1$, $R^{1p}$, $R^2$, $R^3$, $R^4$ and $R^5$ have each the same meaning as defined above, subjecting the compound (VII) to intramolecular ring closure condensation to produce a compound of the formula (IV):

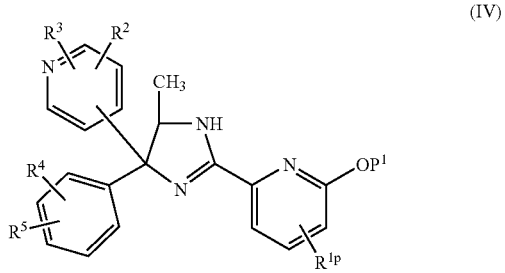

wherein $P^1$, $R^{1p}$, $R^2$, $R^3$, $R^4$ and $R^5$ have each the same meaning as defined above, and optionally removing the protecting group(s) from the compound (IV).

The reaction between a compound of the formula (II) and a compound of the formula (VI) is usually carried out by employing 0.5 moles to excess moles, preferably 1 mole to 2 moles of the compound (VI), relative to 1 mole of the compound (II).

The reaction is usually carried out in an inert solvent, and preferable examples of such solvent are methylene chloride, chloroform, tetrahydrofuran, dimethylformamide, pyridine, etc., or a mixture thereof and the like.

The above reaction is preferably carried out in the presence of a condensing reagent, and examples of such condensing reagent are N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)phosphonium hexafluorophosphate, benzotriazol-1-yloxy-tris-pyrrolidinophosphonium hexafluorophosphate, diphenylphosphoric azide, 1,1-carbonyldiimidazole and the like.

Such condensing reagents can be usually used in 1 mole to excess moles, preferably 1 to 3 moles, relative to 1 mole of a compound of the formula (II).

The reaction temperature is usually from −20° C. to the boiling point of the solvent used in the reaction, preferably from 0° C. to 60° C.

The reaction time is usually 30 minutes to 3 days, preferably 1 to 24 hours.

A usual workup procedure is applied after completion of the reaction to obtain a crude product of a compound of the formula (VII). The resulting compound of the formula (VII) may be, with or without purification according to the conventional manner, subjected to intramolecular ring closure condensation.

The intramolecular ring closure condensation for preparing a compound of the formula (IV) from the compound (VII) is usually carried out in the absence of a solvent or in the presence of an inert solvent.

Preferable examples of such inert solvents are ethanol, propanol, butanol, pentanol, 1,4-dioxane, dimethoxyethane, dimethylformamide, dimethyl sulfoxide, benzene, toluene, xylene, etc., and a mixture thereof and the like.

The reaction temperature is usually from room temperature to the boiling point of the solvent used, preferably from 80° C. to 190° C.

The reaction time is usually 5 hours to 7 days, preferably 12 hours to 3 days.

The above ring closure may be carried out in the presence of a dehydrating reagent or a catalytic-amount of Lewis acid. Examples of the dehydrating reagent are phosphorus oxychloride, phosphorus pentachloride, polyphosphoric acid, thionyl chloride and the like. Examples of the Lewis acid are scandium trifluoromethanesulfonate, yttrium trifluoromethanesulfonate, lanthanum trifluoromethanesulfonate, lanthanide trifluoromethanesulfonate and the like. The reaction is effected in the absence of a solvent or preferably in the presence of a solvent such as methylene chloride, chloroform, benzene, toluene, xylene, etc. or a mixture thereof.

The amount of the dehydrating agent used is usually 1 mole to excess moles, preferably 2 to 10 moles, relative to 1 mole of a compound of the formula (VII), and the amount of the Lewis acid used is 1 mole % to 50 mole %, preferably 5 mole % to 30 mole %.

In general, the reaction temperature is preferably from room temperature to the boiling point of the solvent used.

The reaction time is from one hour to 7 days, preferably from 5 hours to 3 days.

A compound of the formula (I) can be produced by working up a reaction mixture in the usual way after removal of the said protecting group(s) when the product has a protecting group after completion of the reaction, or by working up the mixture directly in the usual way when the protecting group is absent.

The removal of the protecting group(s) and the workup procedure may be carried out according to the method described in the above Production Process 1.

The compounds of the formula (I) may be readily isolated and purified by the conventional separation technique, and examples of such technique are solvent extraction, recrystallization, column chromatography, preparative thin layer chromatography and the like.

These compounds can be converted into the pharmaceutically acceptable salts by a conventional method, and on the contrary, the conversion of the salts into free compounds can also be carried out according to a conventional method.

The compounds of the formulae (II), (III), (V) and (VI) are commercially available, or can be prepared according to common methods or analogous methods thereto, or the methods shown in Examples and Reference Examples, optionally employed in combination.

The utility of compounds of the present invention as a medicament is proved by the following pharmacological tests.

Pharmacological Test 1 (NPY Binding Inhibition Test)

cDNA sequence encoding human NPY Y5 receptor (c.f. International patent publication WO96/16542) was cloned into expression vectors pcDNA3, pRc/RSV (made by Invitrogen Inc.) and pCI-neo (made by Promega Inc.). The expression vectors thus obtained were transfected to host cells COS-7, CHO and LM(tk−) (American Type Culture Collection) by cationic lipid method (Proceedings of the National Academy of Sciences of the United States of America, vol. 84: p. 7413(1987)) to give NPY Y5 receptor expression cells.

A membrane sample prepared from the cells which expressed NPY Y5 receptor was incubated together with a test compound and [$^{125}$I]peptideYY (made by NEN) (20,000 cpm) in an assay buffer (25 mM Tris buffer, pH7.4, containing 10 mM magnesium chloride, 1 mM phenylmethylsulfonyl fluoride, 0.1% bacitracin and 0.5% bovine serum albumin) at 25° C. for 2 hours, then filtered through a glass filter GF/C and washed with 5 mM Tris buffer (pH7.4) containing 0.3% BSA. The radioactivity of the cake on the glass filter was measured. Non-specific binding was measured in the presence of 1 μM peptide YY, and a 50% Inhibitory Concentration ($IC_{50}$) of the test compound against specific peptide YY binding was determined (Endocrinology, vol. 131: p. 2090(1992)). The result revealed that $IC_{50}$ of the compound of Example 1 was 2.8 nM.

As shown above, the compounds of this invention potently inhibited peptide YY (NPY analogue) binding to NPY Y5 receptors.

Pharmacological Test 2 (Antagonistic Effect on D-Trp$^{34}$NPY-Induced Feeding Behavior)

A chronic guide cannula (26 gauge, length 11 mm) was inserted stereotaxicly into the third cerebral ventricle of male SD rats (7–8 weeks old, 200–300 g) anesthetized with ketamine/xylazine (single intraperitoneal administration of 74 and 11 mg/kg) and fixed by dental resin. The tip of the guide cannula was located 2.2 mm posterior to bregma, 8 mm ventral to the skull surface, and on the midline. After about 1-week recovery period, D-Trp$^{34}$NPY (NPY analogue, 1 μg/0.4 μL/head, artificial cerebrospinal fluid containing 0.05% bovine serum albumin) was injected into the third ventricle. A test compound suspended in 0.5% aqueous methylcellulose solution was administered orally 2 hours before the administration of D-Trp$^{34}$NPY, and the food consumption was measured 2 hours after the administration of D-Trp$^{34}$NPY.

The results revealed that 10 mg/kg of the compound of this invention significantly suppressed the increase in food consumption induced by D-Trp$^{34}$NPY which was administered to the third ventricle.

Pharmacological Test 3 (Pharmacokinetics Test)

A test compound was orally or intravenously administered to male SD rats (7–10 weeks old, 200–400 g) under the overnight fasting condition. About 100 μL of blood was collected from the tail vein by heparinized capillary at designated time. The blood was centrifuged (4° C., 6,000 r.p.m., 10 minutes) to obtain the plasma. Three-fold amount of ethanol containing an internal standard was added to plasma. The mixture was stirred, allowed to stand at −20° C. for 20 minutes, and then centrifuged (4° C., 10,000 r.p.m., 10 minutes). The supernatant was analyzed by LC/MS/MS, and the concentration of the test compound in the plasma was measured using a relative calibration curve.

The results revealed that the bioavailability of the compound of Example 1 was 51% and its half-life in the plasma was 2.5 hours.

Pharmacological Test 4 (Brain/Cerebrospinal Fluid Transport Test)

A test compound was orally or intravenously administered to male SD rats (7–10 weeks old, 200–400 g), and whole blood was collected from the abdominal aorta using a heparin-treated syringe under the ether anesthesia at designated time. Then, the head skin was cut out, and a dental 30 G needle was inserted between the cervical vertebrae, and it was further inserted into the cavum subarachnoideum. After 50 to 100 μL cerebrospinal fluid had been collected by a 1 ml-syringe through a tube connected to the dental 30 G needle, the brain was extracted. The blood sample was centrifuged (4° C., 6,000 r.p.m., 10 minutes) to obtain the plasma, and 3-fold amount of ethanol containing an internal standard was added and stirred. The brain sample was homogenized after addition of 2 ml water, and an aliquot of the homogenate was taken and 3-fold amount of ethanol containing an internal standard was added and stirred. The cerebrospinal fluid was stirred after adding 3-fold amount of ethanol containing an internal standard. These samples were allowed to stand at −20° C. for 20 minutes, and then centrifuged (4° C., 12,000 g, 10 minutes). The supernatant was analyzed by LC/MS/MS, and the concentration of the test compound in the plasma, brain, and cerebrospinal fluid were measured by the method using a relative calibration curve.

The results revealed that concentrations of the compound of Example 1 in the brain, cerebrospinal fluid and plasma were 0.29 nmol/g, 0.106 μM and 2.79 μM, respectively, one hour after oral administration (10 mg/kg).

Pharmacological Test 5 (General Symptoms Observation)

A test compound was orally administered to male ICR mice (4–6 weeks old) under the overnight fasting condition, and general symptoms were observed 0.5, 1, 2, 3, 4 and 24 hours after the administration. The following 28 items were observed: stereotypy, glooming, vocalization, exploratory behavior, motor coordination, Straub tail reaction, tremor, convulsion, body posture, piloerection, writhing, palpebral opening, exophthalmos, skin color, respiratory rate, urination, defecation, salivation, lacrimation, startle response, aggression, grip strength, corneal reflex, body temperature, body tone, righting reflex, pain response and death.

The result revealed that the administration of the compound of Example 1 (100 mg/kg) did not affect general symptoms.

Pharmacological Test 6 (Gastrointestinal Motility)

A test compound was orally administered to male ICR mice (4–6 weeks old) under the overnight fasting condition and, one hour later, 0.5% charcoal suspension (0.1 ml/10 g body weight) was orally administered. One hour after the administration of the charcoal, gastrointestinal tracts of the animals were removed, and length of the intestine from pylorus to the point to which charcoal reached was measured to obtain charcoal transportation ratio.

The result revealed that the administration of the compound of Example 1 (100 mg/kg) did not affect gastrointestinal motility.

Pharmacological Test 7 (Canine Cardiac Function)

The left femoral artery and vein of male beagle dogs (age: 9 months or older, weight: 10–15 kg) under anesthesia with isoflurane and artificial respiration were respectively cannulated for determination of arterial pressure and for administration of drugs. A tip catheter pressure transducer was placed in the left ventricle from the left carotid artery for determination of the left ventricular pressure. A Swan-Ganz catheter was placed in the pulmonary artery from the jugular vein via the right ventricle for determination of the pulmonary artery pressure, right atrium pressure and cardiac output. A transit doppler flow probe was attached to the right femoral artery for determination of the femoral blood flow. After completion of the operation, a solvent was administered from the cannula in the vein, followed by administration of a drug to be tested. Each parameter was determined just after the administration, and 10, 20, 30 and 60 minutes after the administration. The parameters determined were artery pressure, left ventricular pressure, pulmonary artery pressure, right atrium pressure, cardiac output, femoral blood flow, heart rate, electrocardiogram, left ventricular contractile performance (first differential of the left ventricular pressure), total peripheral vascular resistance, body temperature and arterial blood gas.

The result revealed that the administration of the compound of Example 1 (3 mg/kg and 10 mg/kg) did not affect canine cardiac function.

The compounds of the formula (I) can be administered orally or parenterally and, by formulating into a suitable administrable form, may be administered as a pharmaceutical composition for the treatment of various diseases related to NPY, including, for example, cardiovascular disorders such as angina, acute or congestive heart failure, myocardial infarction, hypertension, nephropathy, electrolyte abnormality, vasospasm, etc., nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, gout, fatty liver, etc., genital or reproductive disorders such as infertility, preterm labor, sexual dysfunction, etc., gastro-intestinal disorders, respiratory disorders, inflammatory diseases or glaucoma, and the like. In clinical use, the compounds of this invention may be administered after being formulated, together with pharmaceutically acceptable additives, into an appropriate preparation according to the mode of administration. As for said additives, those which are usually used in the field of pharmaceutical formulation, for example, gelatin, lactose, sucrose, titanium oxide, starch, crystalline cellulose, hydroxypropyl methylcellulose, carboxymethylcellulose, corn starch, microcrystalline wax, white petrolatum, magnesium methasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropyl cyclodextrin, etc. may be used.

The formulations prepared by mixing the compound of the present invention with said additives include, for example, solid preparations (e.g. tablets, capsules, granules, powder, suppositories); or liquid preparations (e.g. syrups, elixirs, injections). Such preparations may be formulated according to the techniques well-known in the art of pharmaceutical formulation. Liquid preparations may be in the form of preparations which are dissolved or suspended in water or other appropriate media when used. In the case of injectable preparations, in particular, they may be dissolved or suspended in physiological saline or glucose solution if necessary, optionally together with a buffer and a preservative.

All the said preparations may contain 1.0 to 100 wt. %, preferably 1.0 to 60 wt. % of compounds of the present invention and may also contain other therapeutically effective compound(s).

The compounds of the present invention can be used in combination with other agents useful for treating metabolic disorders and/or eating disorders. The individual component of such combinations can be administered separately at different times or concurrently in divided or single combination forms during the course of therapy. The present invention is therefore to be understood as embracing all such regimes of simultaneous or divided administration and the term "administering" is to be interpreted accordingly. The scope of combinations of the compounds of this invention with other agents useful for treating metabolic disorders and/or eating disorders includes in principle any combination of any pharmaceutical composition useful for treating metabolic disorders and/or eating disorders.

When compounds of this invention are used clinically, for example, a daily dose for an adult is 0.01–100 mg/kg, preferably 0.03–1 mg/kg with simultaneous or divided administration when administered orally, and 0.001–10 mg/kg, preferably 0.001–0.1 mg/kg with simultaneous or divided administration when administered parenterally, though the dose and the frequency of dosage may vary depending upon the sex, age, body weight, the degree of symptoms and the kind and range of the desired treatment effects.

An ordinarily skilled physician, veterinarian or clinician can readily determine and prescribe the effective amount of the drug required to prevent, suppress or arrest the progress of diseases.

BEST MODE FOR CARRYING OUT THE INVENTION

The present invention is further described in detail with reference to the following Examples and Reference Examples, but the invention should in no way be restricted thereby.

The compounds with the symbol * in the chemical formulae indicate that the stereo configuration on the asymmetric carbon atom with the symbol * is substantially of a single compound.

The melting points were measured with MP-S3 model (manufactured by Yanagimoto Seisakusho Co. Ltd.) and described without correction.

EXAMPLE 1

Preparation of 6-[(4R,5S)-4-(4-fluorophenyl)-4-(2-fluoro-4-pyridyl)-5-methyl-2-imidazolin-2-yl]-2(1H)-pyridinone (1) Preparation of N-[(1S,2R)-2-amino-2-(4-fluorophenyl)-2-(2-fluoro-4-pyridyl)-1-methylethyl]-6-oxo-1,6-dihydro-2-pyridinecarboxamide (1R,2S)-1-(4-fluorophenyl)-1-(2-fluoro-4-pyridyl)-1,2-propanediamine (25.6 g) and 6-hydroxy-2-pyridinecarboxylic acid (14.9 g) were dissolved in a mixture of pyridine (250 mL) and dichloromethane (250 mL). To the solution was added 1-(3-dimethylaminopropyl)-3-ethylcarbodiimide hydrochloride (24.3 g), and the mixture was stirred at room temperature for 1.5 hours. The reaction mixture was concentrated in vacuo, and the residue was dissolved in ethyl acetate. The solution was washed successively with water and saturated brine, dried over anhydrous sodium sulfate, and filtered to remove the sodium sulfate. The organic solvent was evaporated in vacuo, and the residue was purified by column chromatography on silica gel (chloroform:methanol=10:0→10:1) to give the objective compound as a pale yellow solid. The solid was suspended in ethyl acetate, and to this was added 1N sodium hydroxide solution. After vigorous stirring at room temperature, the aqueous layer was neutralized with 2N hydrochloric acid, and then the aqueous layer was discarded. The organic layer was washed with saturated brine and dried over anhydrous sodium sulfate. After removal of the sodium sulfate, the organic layer was evaporated in vacuo to give the objective compound (18.4 g) as a pale yellow solid.

(2) Preparation of 6-[(4R,5S)-4-(4-fluorophenyl)-4-(2-fluoro-4-pyridyl)-5-methyl-2-imidazolin-2-yl]-2(1H)-pyridinone (Crystal Form A)

N-[(1S,2R)-2-amino-2-(4-fluorophenyl)-2-(2-fluoro-4-pyridyl)-1-methylethyl]-6-oxo-1,6-dihydro-2-pyridine-carboxamide (16 g) was suspended in toluene (400 mL), and the suspension was heated under reflux for 10 hours while removing water azeotropically. The reaction mixture was concentrated in vacuo and the residue was purified by column chromatography (ethyl acetate:methanol=100:0→10:1) to give the title compound as a yellow oil. The yellow oil was dissolved in isopropanol (80 mL), and to this solution was added water (130 mL) at room temperature. The solution was allowed to stand at room temperature for 3 hours to give a colorless crystal, which was then collected by filtration. The crystal was suspended in water (500 mL) and the suspension was stirred at room temperature for 14 hours. The resulting crystal was collected again by filtration and dried in vacuo at 30° C. for 24 hours to give the title compound (crystal form A)(11.2 g) as a colorless massive crystal (m.p. 125–126° C.).

$[\alpha]_D^{25}$: −273° (c 1.0, ethanol)

powder X-ray diffraction analysis

| 2θ | Relative Intensity* |
|---|---|
| 8.3 | 100 |
| 10 | 24 |
| 12.3 | 7 |
| 13.2 | 8 |
| 13.8 | 15 |
| 15.5 | 10 |
| 16.6 | 14 |
| 17.8 | 15 |
| 18.8 | 35 |
| 20.1 | 12 |
| 20.6 | 11 |
| 20.9 | 20 |
| 21.3 | 24 |
| 22.2 | 10 |
| 22.5 | 8 |
| 22.8 | 20 |
| 24.4 | 10 |
| 24.8 | 23 |
| 25.1 | 68 |
| 26.9 | 10 |
| 28 | 10 |
| 28.2 | 13 |
| 29.2 | 5 |
| 29.6 | 12 |
| 30.8 | 9 |
| 32.1 | 11 |
| 32.4 | 8 |
| 35.9 | 5 |
| 40.1 | 5 |
| 43.6 | 10 |

*relative value to the maximum intensity (set to 100)

The above powder X-ray diffraction analysis data were measured by an automatic X-ray apparatus RINT-Ultima+ System (2KW) (manufactured by Rigaku International Corporation). The analysis methods were as follows:
X-ray radiation source: Cu,
tube voltage/tube current: 40 kV/30 mA,
monochrometer: automatic monochrometer,
goniometer: wide angle goniometer,
scan step: 0.02 deg.,
scan speed: 2.00 deg./min.,
divergence slit (DS): 1 deg.,
scattering slit: 1 deg.,
receiving slit: 0.15 mm,
measured temperature: room temperature

(3) Preparation of Colorless Platelet-Like Crystal of 6-[(4R,5S)-4-(4-fluorophenyl)-4-(2-fluoro-4-pyridyl)-5-methyl-2-imidazolin-2-yl]-2(1H)-pyridinone (Crystal Form A)

The colorless massive crystal (crystal form A)(2 mg) obtained in the above procedure (2) was dissolved in ethanol (1 mL), and then water (about 200 μL) was added. A mouth of the container containing the solution was covered with Parafilm, and several holes were opened in the Parafilm with a needle. The solution was kept at room temperature for 3 days to give the title crystal.

(4) Preparation of 6-[(4R,5S)-4-(4-fluorophenyl)-4-(2-fluoro-4-pyridyl)-5-methyl-2-imidazolin-2-yl]-2(1H)-pyridinone (Crystal Form B)

The yellow oil (1.21 g) obtained in the above procedure (2) was dissolved in ethyl acetate (100 mL), and then n-heptane (about 300 mL) was added thereto. After allowing the solution to stand at 0° C. for 2 hours, the resulting colorless crystal was collected by filtration. The crystal was dried in vacuo at 40° C. for 17 hours to give the title compound (crystal form B)(0.84 g) as a colorless massive crystal (m.p. 115–118° C.).

powder X-ray diffraction analysis

| 2θ | Relative Intensity* |
|---|---|
| 8.2 | 78 |
| 9.3 | 27 |
| 9.5 | 33 |
| 10.4 | 22 |
| 10.9 | 31 |
| 13.1 | 65 |
| 13.8 | 32 |
| 15.3 | 21 |
| 16.5 | 28 |
| 17 | 20 |
| 17.1 | 21 |
| 17.9 | 53 |
| 18.2 | 100 |
| 18.9 | 42 |
| 20.4 | 79 |
| 20.7 | 80 |
| 21 | 60 |
| 21.9 | 28 |
| 23.7 | 22 |
| 23.9 | 26 |
| 24.6 | 21 |
| 25 | 48 |
| 25.4 | 34 |
| 25.8 | 34 |
| 26.3 | 26 |
| 27.3 | 21 |
| 27.7 | 24 |
| 29 | 65 |
| 30.8 | 19 |
| 33.1 | 19 |

*relative value to the maximum intensity (set to 100)

The above data of powder X-ray diffraction analysis were measured under the same conditions as in Example 1(2).

(5) Preparation of 6-[(4R,5S)-4-(4-fluorophenyl)-4-(2-fluoro-4-pyridyl)-5-methyl-2-imidazolin-2-yl]-2(1H)-pyridinone (crystal form A) (Alternative Method)

The crystal (crystal form B) (24 mg) obtained in the above procedure (4) was suspended in water (1 mL) and the solution was stirred at room temperature for 3 days. The solution was centrifuged at 10,000 rpm for 10 minutes to remove the supernatant. The resulting crystal was dried in vacuo to give the title compound (crystal form A) as a colorless prism-like crystal.

EXAMPLE 2

Preparation of 5-fluoro-6-[(4S,5S)-4-(4-fluorophenyl)-4-(6-fluoro-3-pyridyl)-5-methyl-2-imidazolin-2-yl]-2(1H)-pyridinone According to the method of Example 1, optically active (2S)-1-(4-fluorophenyl)-1-(6-fluoro-3-pyridyl)-1,2-propanediamine described in Reference Example 5–1 of WO 01/62738 was reacted with 3-fluoro-6-oxo-1,6-dihydro-2-pyridinecarboxylic acid to give the title compound.

$^1$HNMR (400 MHz, CDCl$_3$, δppm) 0.89 (3H, d, J=6.8 Hz), 4.85 (1H, q, J=6.8H z), 6.77 (1H, dd, J=3.6 Hz, 9.2 Hz), 7.05 (1H, dd, J=2.4, 8.0 Hz), 7.06–7.11 (2H, m), 7.29–7.33 (2H, m), 7.57 (1H, t, J=9.6 Hz), 8.01–8.06 (1H, m), 8.33 (1H, d, J=2.4 Hz)

$[α]_D^{25}$: −304° (c 1.0, ethanol)

EXAMPLE 3

Preparation of Optically Active

6-[(5S)-4-(4-fluorophenyl)-5-methyl-4-(6-trifluoromethyl-3-pyridyl)-2-imidazolin-2-yl]-3-methyl-2(1H)-pyridinone using the diamine of Reference Example 4 as a starting material To a solution of 2-benzyoxy-6-cyano-3-methylpyridine (90 mg) in methanol was added sodium methoxide (4 mg), and the mixture was stirred at 50° C. for 48 hours. After the temperature of the reaction mixture was lowered to room temperature, methanesulfonic acid (44 mg) was added thereto, followed by stirring at room temperature for 30 minutes. The diamine (89 mg) obtained in Reference Example 4 was added to the reaction mixture, and the mixture was stirred at 50° C. for 60 hours. After removal of the organic solvent by evaporation in vacuo, the resulting residue was dissolved in chloroform. The solution was washed with saturated aqueous sodium bicarbonate, and dried over anhydrous sodium sulfate. After removal of the sodium sulfate by filtration, the organic solvent is evaporated of f in vacuo. The residue was purified by column chromatography on silica gel (hexane:ethyl acetate=9:1) to give the objective benzyl compound (103 mg) as a colorless oil. The benzyl compound (103 mg) obtained above was dissolved in trifluoroacetic acid (5 mL), and the solution was stirred at room temperature for 16 hours, then concentrated in vacuo to remove the trifluoroacetic acid. The residue was dissolved in chloroform, and the solution was washed with saturated aqueous sodium bicarbonate, and dried over anhydrous sodium sulfate. After removal of the sodium sulfate by filtration, the organic solvent was evaporated off in vacuo. The residue was purified by column chromatography on silica gel (chloroform:methanol=9:1) to give the title compound (51 mg) as a white solid.

$^1$HNMR (400 MHz, CD$_3$OD, δppm) 0.89 (3H, d, J=6.4 Hz), 2.16 (3H, s), 4.80–5.00 (1H, m), 6.84 (1H, d, J=7.2 Hz), 7.09 (2H, t, J=8.4 Hz), 7.31 (1H, s), 7.40–7.60 (3H, m), 7.76 (1H, d, J=8.0 Hz), 7.93 (1H, d, J=7.2 Hz), 8.56 (1H, s)

$[α]_D^{25}$: −194° (c 1.0, ethanol)

REFERENCE EXAMPLE 1

Preparation of (1S,2S)-1-(4-fluorophenyl)-1-(2-fluoro-4-pyridyl)-1,2-propanediamine

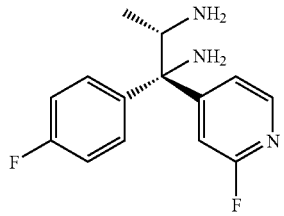

(1) Preparation of t-Butyl N-[(1S)-2-(4-fluorophenyl)-1-methyl-2-oxoethyl]carbamate A solution of t-butyl N-{(1S)-2-[methoxy(methyl)amino]-1-methyl-2-oxoethyl}carbamate (50 g) in tetrahydrofuran (700 mL) was gradually added dropwise at 0° C. to a 2.5M 4-fluorophenylmagnesium bromide/tetrahydrofuran solution (300 mL) which had been prepared previously. The mixture was stirred at room temperature for 14 hours, cooled to 0° C., and extracted twice with ether after addition of saturated aqueous sodium bicarbonate. The organic layer was washed successively with saturated aqueous sodium bicarbonate and saturated brine, and dried over anhydrous sodium sulfate. After removal of the sodium sulfate by filtration, the organic solvent was evaporated off in vacuo. The resulting residue was purified by column chromatography on silica gel (C-300; hexane:ethyl acetate=4:1) to give the title compound.

(2) Preparation of (1S,2S)-1-(4-fluorophenyl)-1-(2-fluoro-4-pyridyl)-1,2-propanediamine Condensation of t-butyl N-[(1S)-2-(4-fluorophenyl)-1-methyl-2-oxoethyl]carbamate with (R)-(+)-2-methyl-2-propanesulfinamide in the presence of a dehydrating agent gave t-butyl N-[(1S)-2-[((R)-t-butylsulfinyl)imino]-2-(4-fluorophenyl)-1-methylethyl]carbamate. To a solution of the sulfinylimine compound (80 mg) in toluene (2 mL) was added 1.0M trimethylaluminum/hexane solution (0.43 mL) at −78° C., followed by stirring for 5 minutes. The resulting solution was gradually added dropwise at −78° C. to a solution of 2-fluoro-4-pyridyllithium, which had been prepared by reacting 4-fluoro-2-bromopyridine (114 mg) with 1.56M butyllithium/hexane solution (0.46 mL) in diethyl ether (3 mL) at −78° C. After completion of the dropping, tetrahydrofuran (3 mL) was added to the reaction mixture, followed by stirring at −78° C. for 2.5 hours. Saturated brine was added to the reaction mixture and the temperature was elevated to room temperature. The reaction solution was filtered through a Celite pad, and the organic layer in the filtrate was dried over anhydrous magnesium sulfate. After removal of the magnesium sulfate by filtration, the organic solvent was evaporated off in vacuo. The residue was purified by column chromatography on silica gel (C-300; hexane:ethyl acetate=2:1) to give t-butyl N-[(1S,2S)-2-[(t-butylsulfinyl)amino]-2-(4-fluorophenyl)-2-(2-fluoro-4-pyridyl)-1-methylethyl]carbamate (49 mg). The product was treated with 4N hydrogen chloride/dioxane solution to give the optically active diamine indicated in the title.

¹HNMR (300 MHz, CDCl₃, δppm): 1.03 (3H, d, J=6.3 Hz), 1.91 (4H, brs), 4.10 (1H, q, J=6.3 Hz), 6.98–7.48 (6H, m), 8.12 (1H, d, J=5.1 Hz)

REFERENCE EXAMPLE 2

Preparation of (1R,2S)-1-(4-fluorophenyl)-1-(2-fluoro-4-pyridyl)-1,2-propanediamine

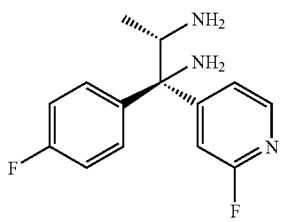

According to the procedure of Reference Example 1, t-butyl N-[(1S)-2-[((R)-t-butylsulfinyl)imino]-2-(2-fluoro-4-pyridyl)-1-methylethyl]carbamate was reacted with 4-fluorophenyllithium, and subsequent deprotection under an acidic condition gave the title diamine.

¹HNMR (300 MHz, CDCl₃, δppm): 0.98 (3H, d, J=6.4 Hz), 4.07 (1H, q, J=6.4 Hz), 6.98–7.07 (2H, m), 7.10 (1H, s), 7.24 (1H, dt, J=5.4 Hz,1.7 Hz), 7.48-7.58 (2H, m), 8.11 (1H, d, J=5.3 Hz)

REFERENCE EXAMPLE 3

Preparation of Optically Active (2S)-1-(4-fluorophenyl)-1-(6-trifluoromethyl-3-pyridyl)-1,2-propanediamine

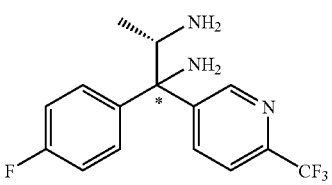

According to the procedure of Reference Example 1, t-butyl N-[(1S)-2-[((R)-t-butylsulfinyl)imino]-2-(4-fluorophenyl)-1-methylethyl]carbamate was reacted with 6-trifluoromethyl-3-pyridyllithium, and subsequent deprotection under an acidic condition gave the title diamine.

¹HNMR (300 MHz, CDCl₃, δppm): 1.03 (3H, d, J=6.3 Hz), 4.14 (1H, q, J=6.3 Hz), 7.01 (2H, t, J=9.0 Hz), 7.42–7.47 (2H, m), 7.61 (1H, d, J=8.1 Hz), 8.10 (1H, dd, J=2.1 Hz,8.4 Hz), 8.90 (1H, d, J=2.1 Hz)

REFERENCE EXAMPLE 4

Preparation of Optically Active (2S)-1-(4-fluorophenyl)-1-(6-trifluoromethyl-3-pyridyl)-1,2-propanediamine (Epimer in the first position of the compound of Reference Example 3)

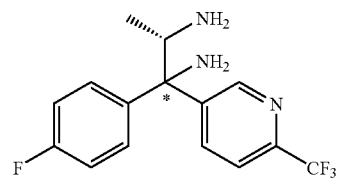

According to the procedure of Reference Example 1, t-butyl N-[(1S)-2-[((R)-t-butylsulfinyl)imino]-1-methyl-2-(6-trifluoromethyl-3-pyridyl)ethyl]carbamate was reacted with 4-fluorophenyllithium, and subsequent deprotection under an acidic condition gave the title diamine.

¹HNMR (400 MHz, CDCl₃, δppm): 0.99 (3H, d, J=6.4 Hz), 4.12 (1H, q, J=6.4 Hz), 7.00 (2H, d, J=10.0 Hz), 7.50–7.60 (2H, m), 7.61 (1H, d, J=8.0 Hz), 8.03 (1H, d, J=8.0 Hz), 8.83 (1H, s)

REFERENCE EXAMPLE 5

Preparation of 2-benzyloxy-6-cyano-3-methylpyridine

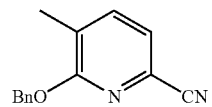

To a solution of 2-bromo-6-cyano-3-methylpyridine (272 mg) and benzyl alcohol (156 mg) in tetrahydrofuran (20 mL) was added sodium hydride (40 mg), and the mixture was heated under reflux for one hour. The reaction mixture was cooled to room temperature, diluted with ethyl acetate, washed successively with saturated aqueous sodium bicarbonate and saturated brine, and dried over anhydrous sodium sulfate. After removal of the sodium sulfate by filtration, the organic solvent was evaporated off in vacuo. The residue was purified by column chromatography on silica gel (hexane:ethyl acetate=19:1) to give the title compound (161 mg) as a colorless liquid.

¹HNMR (400 MHz, CDCl₃, δppm) 2.28 (3H, s), 5.40 (2H, s), 7.20–7.30 (1H, m), 7.30–7.40 (3H, m), 7.40–7.50 (3H, m)

REFERENCE EXAMPLE 6

Preparation of 3-fluoro-6-oxo-1,6-dihydro-2-pyridinecarboxylic acid

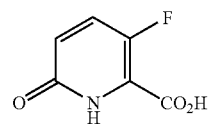

To a solution of 3-fluoro-2-methoxycarbonylpyridine-N-oxide (5.00 g) in dimethylformamide (12 mL) was gradually added anhydrous trifluoroacetic acid (24 mL) in an ice-bath, and the mixture was stirred at room temperature for 3 hours. After removal of the solvent by evaporation in vacuo, saturated brine was gradually added to the residue in an ice-bath, and then the mixture was extracted with ethyl acetate. The organic layer was dried over anhydrous sodium sulfate and then the sodium sulfate was removed by filtration. The organic solvent was removed by evaporation in vacuo to give a pale yellow solid, which was then washed with diethyl ether. The solid was dried in vacuo to give the title methyl ester compound as a pale yellow solid (2.73 g). The methyl ester compound was hydrolyzed under a basic condition to give the title compound (2.05 g) as a colorless solid.

$^1$HNMR (400 MHz, DMSO-$d_6$, δppm): 6.81 (1H, dd, J=3.2, 9.2 Hz), 7.66 (1H, t, J=9.2 Hz)

FORMULATION EXAMPLE 1

20.0 grams of the compound of Example 1, 417 grams of lactose, 80 grams of crystalline cellulose and 80 grams of partial α-starch were blended with a V-cone blender. To the mixture was added magnesium stearate (3.0 g) and the whole was blended. The blended powder was compressed into 3,000 tablets by conventional procedure so that each tablet has a weight of 150 mg and a diameter of 7.0 mm.

| Content of one tablet (150 mg) | |
| --- | --- |
| compound of Example 1 | 5.0 mg |
| lactose | 104.25 mg |
| crystalline cellulose | 20.0 mg |
| partial alpha-starch | 20.0 mg |
| magnesium stearate | 0.75 mg |

FORMULATION EXAMPLE 2

10.8 grams of hydroxypropylcellulose 2910 and 2.1 grams of polyethylene glycol 6000 were dissolved in purified water (172.5 g), and titanium dioxide (2.1 g) was dispersed in the solution to provide a coating liquid. 2,500 tablets prepared in Formulation Example 1 were subjected to spray-coating with the coating liquid using HICOATER-MINI to provide a film coated tablet with a weight of 155 mg.

| Content of one tablet (155 mg) | |
| --- | --- |
| tablet prepared in Formulation Example 1 | 150 mg |
| hydroxypropylcellulose 2910 | 3.6 mg |
| polyethylene glycol 6000 | 0.7 mg |
| titanium dioxide | 0.7 mg |

INDUSTRIAL APPLICABILITY

Compounds of the present invention have NPY antagonistic actions and show, for example, excellent pharmacokinetics such as transport into brain or transport to cerebrospinal fluid, etc., and are very safe. Thus, the compounds of the present invention are useful as pharmaceutical compositions for the treatment of various diseases related to NPY, for example, cardiovascular disorders such as angina, acute or congestive heart failure, myocardial infarction, hypertension, nephropathy, electrolyte abnormality, vasospasm, etc., nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, gout, fatty liver, etc., genital or reproductive disorders such as infertility, preterm labor, sexual dysfunction, etc., gastro-intestinal disorders, respiratory disorders, inflammatory diseases or glaucoma, and the like.

The invention claimed is:

1. A compound of the formula (Ia):

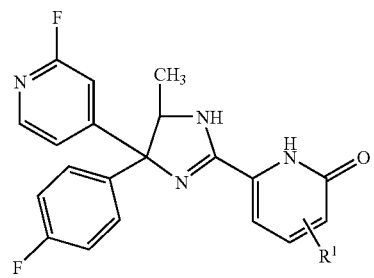

(Ia)

wherein $R^1$ is hydrogen, fluorine or hydroxy, or a salt thereof.

2. A compound of the formula (Ib-1):

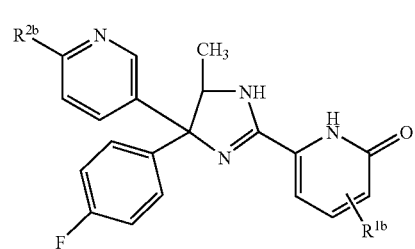

(Ib-1)

in which $R^{1b}$ is halogen or lower alkyl; and $R^{2b}$ is fluorine or trifluoromethyl, or a salt thereof.

3. A compound of the formula (Ib-2):

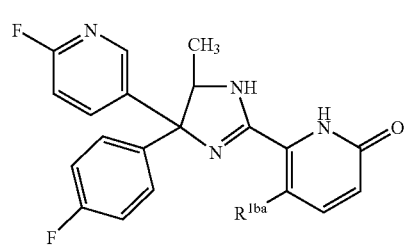

(Ib-2)

wherein $R^{1ba}$ is halogen, or a salt thereof.

4. The compound as claimed in claim 3, wherein the halogen as $R^{1ba}$ is fluorine.

5. A compound of the formula (Ib-3):

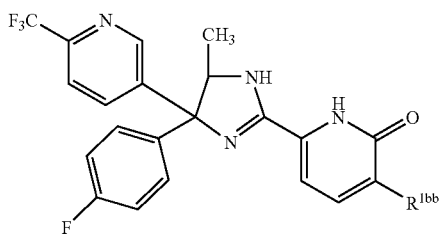

(Ib-3)

in which $R^{1bb}$ is lower alkyl, or a salt thereof.

6. The compound as claimed in claim 5, wherein the lower alkyl as $R^{1bb}$ is methyl.

7. A pharmaceutical composition comprising the compound as claimed in claim 1, or a salt thereof as an active ingredient, together with a pharmaceutically acceptable additive.

8. A pharmaceutical composition comprising the compound as claimed in claim 2, or a salt thereof as an active ingredient, together with a pharmaceutically acceptable additive.

9. A pharmaceutical composition comprising the compound as claimed in claim 3, or a salt thereof as an active ingredient, together with a pharmaceutically acceptable additive.

10. A pharmaceutical composition comprising the compound as claimed in claim 4, or a salt thereof as an active ingredient, together with a pharmaceutically acceptable additive.

11. A pharmaceutical composition comprising the compound as claimed in claim 5, or a salt thereof as an active ingredient, together with a pharmaceutically acceptable additive.

12. A pharmaceutical composition comprising the compound as claimed in claim 6, or a salt thereof as an active ingredient, together with a pharmaceutically acceptable additive.

* * * * *